United States Patent [19]

Josyula et al.

[11] Patent Number: 5,236,926
[45] Date of Patent: Aug. 17, 1993

[54] 9-SUBSTITUTED-8-HALO OR -8-HYDROXY-9-DEAZAGUANINES AS INHIBITORS OR PNP FOR PHARMACEUTICAL COMPOSITIONS

[75] Inventors: Usha Josyula; Jagadish C. Sircar, both of Ann Arbor, Mich.

[73] Assignee: Warner-Lambert Company, Morris Plains, N.J.

[21] Appl. No.: 829,850

[22] Filed: Feb. 3, 1992

[51] Int. Cl.$^5$ .................. A61K 31/505; C07D 471/04
[52] U.S. Cl. .................................. 514/258; 514/234.2; 514/253; 514/254; 544/117; 544/238; 544/280
[58] Field of Search .............. 544/280, 117, 238; 514/258, 234.2, 253

[56] References Cited

U.S. PATENT DOCUMENTS

| | | | |
|---|---|---|---|
| 4,923,872 | 5/1990 | Kostlan et al. | 514/258 |
| 4,985,433 | 1/1991 | Secrist III et al. | 514/258 |
| 4,985,434 | 1/1991 | Secrist III et al. | 514/258 |
| 5,008,265 | 4/1991 | Secrist et al. | 514/258 |
| 5,008,270 | 4/1991 | Secrist et al. | 514/258 |

FOREIGN PATENT DOCUMENTS

WO9010631 9/1990 PCT Int'l Appl.
WO9106548 5/1991 PCT Int'l Appl.

OTHER PUBLICATIONS

CA 113(23): 204453m (1990).

Primary Examiner—Thurman K. Page
Assistant Examiner—Jyothsna Venkat
Attorney, Agent, or Firm—Ronald A. Daignault

[57] ABSTRACT

The present invention is novel 9-substituted-8-hydroxy or -8-halo-9 deazaguanines and pharmaceutical compositions and methods of use therefor. The derivatives are inhibitors of purine nucleoside phosphorylase selectively cytotoxic to T-cells but not to B-cells in the presence of 2'-deoxyguanosine and, therefore, are for use in the treatment of autoimmune diseases, gout, psoriasis or rejection of transplantation.

18 Claims, No Drawings

9-SUBSTITUTED-8-HALO OR -8-HYDROXY-9-DEAZAGUANINES AS INHIBITORS OR PNP FOR PHARMACEUTICAL COMPOSITIONS

BACKGROUND OF THE INVENTION

Various purine derivatives are known including 9-deazaguanines such as 8-desamino-9-deazaguanines and their derivatives having activity as inhibitors of purine nucleoside phosphorylase (PNp-4). For example, see U.S. Pat. No. 4,923,872 and related patents, and the patent application W09106-548A and W09010-631A as well as U.S. Pat. Nos. 5,008,270; 5,008,265; 4,985,434; and 4,985,433. These are incorporated by reference to show related references as cited in each.

The previous disclosures differ from the present invention of the Formula I at least by the 8-halo or 8-hydroxy substituent now found to provide PNP inhibitor activity.

SUMMARY OF THE INVENTION

The present invention relates to a compound of the Formula (I)

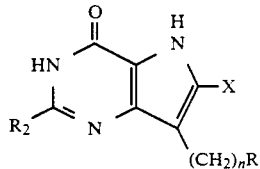

wherein $R_2$ is hydrogen, chloro, fluoro, NHR' wherein R' is hydrogen or alkyl, or NHR" wherein R" is acyl of from two to six carbons; n is an integer of zero through four, preferably one; and R is an optionally substituted cyclic group as defined hereinafter; X is F, Cl, Br, I, or OH; or a pharmaceutically acceptable acid or base addition salt thereof.

The present invention also includes methods of manufacturing and a pharmaceutical composition for treating diseases that are 1) recognized as autoimmune diseases; such as arthritis, systemic lupus erythematosus, inflammatory bowel diseases, juvenile diabetes, myasthenia gravis, multiple sclerosis, gout and gouty arthritis, as well as 2) psoriasis, 3) viral infections responsive to agents that are cytotoxic to T-cells, and 4) cancer such as is responsive to agents that are cytotoxic to T-cells, or 5) rejection of transplantation, comprising an immunomodulator, antipsoriatic, antiviral, anticancer, or antirejection effective amount; such as a cytotoxic to T-cell amount, of a compound of the Formula I or the Formula Q with a pharmaceutically acceptable carrier. Thus, the invention may also be said to be a method to manufacture the pharmaceutical composition for treating the diseases as set out above.

The invention is also a method of treating an autoimmune disease, psoriasis, viral infection and cancer or rejection of transplantation susceptible to agents that are cytotoxic to T-cells comprising administering to a host, such as a mammal, including a human, suffering from an autoimmune disease, cancer, psoriasis, or transplantation rejection advantageously affected by T-cell toxicity comprising administering an effective amount of a compound of the Formula I or the Formula Q in unit dosage form. It is understood, an ordinarily skilled physician would begin treatment with a nontoxic and less than effective amount and increase the dose until the desired effect is obtained exercising care to administer an amount less than the amount toxic to the host of the disease. The present invention also includes novel intermediates as follows: (1) A compound of the Formula (II)

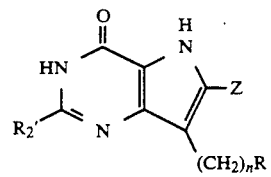

wherein $R'_2$ is hydrogen or NHR', Z is $N_2{}^+PF_6{}^-$, or $N_2{}^+BF_4{}^-$ or $N_2{}^+Cl^-$ and R is as defined above.

The novel processes of the present invention are generally as follows:

(A) A process for the preparation of a compound of the Formula I comprising treating a compound of the Formula II wherein $R'_2$ is H or NHR' wherein R', n, and R are as defined above with 1) potassium iodide in a solvent such as methanol, ethanol or the like to obtain a compound of the Formula I wherein X is I, at about room temperature, i.e., 20° C. to 25° C.; 2) by heating either neat or in a solvent such as diphenylether the compound of Formula II wherein Z is $N_2{}^+BF_4{}^-$ or $N_2{}^+ {}^{PF}6^-$ to obtain a compound of Formula I wherein X is F, at about 200° C. to 220° C., preferably about 200° C.; 3) a hot solution of CuX' and HX' wherein X' is bromo or chloro to obtain a compound of the Formula I wherein X is Br or Cl, at about 60° C. to 80° C., preferably about 70° C.; or, 4) water containing an acid such as $H_2SO_4$ to obtain a compound of the Formula I wherein X is OH, at about 60° C. to 80° C., preferably about 70° C.; optionally acylating the $NH_2$, if desired, to obtain a compound of the Formula I wherein $R_2$ is NHR" wherein R" is acyl of from two to four carbons;

(B) A process for the preparation of a compound of the Formula II wherein $R'_2$ is H or $NH_2$ and n and R are as defined above, comprising treating a compound of the Formula (III)

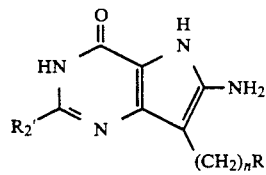

wherein $R'_2$ is hydrogen or NHR' wherein R' is as defined above and n and R are as defined above;

with $HPF_6$, $HBF_4$ or HCl in methanol, ethanol, or the like and then with an aqueous solution of $NaNO_2$ at about 0° C.

See Scheme I hereinafter.

Under certain circumstances it may be necessary to protect either the N or O of intermediates in the above-noted process with suitable protecting groups which are known. Introduction and removal of such suitable oxygen and nitrogen protecting groups are well known in the art of organic chemistry; see for example, (1) "Protective Groups in Organic Chemistry," J. F. W. McOmie, ed., (New York, 1973), pp 43ff, 95ff; (2) J. F. W. McOmie, *Advances in Organic Chemistry*, Vol. 3, 191–281 (1963); (3) R. A. Borssonas, *Advances in Organic Chemistry*, Vol. 3, 159–190 (1963); and (4) J. F. W. McOmie, *Chem. & Ind.*, 603 (1979).

Examples of suitable oxygen protecting groups are benzyl, t-butyldimethylsilyl, methyl, isopropyl, ethyl, tertiary butyl, ethoxyethyl, and the like. Protection of an N—H containing moiety is necessary for some of the processes described herein for the preparation of compounds of this invention. Suitable nitrogen protecting groups are benzyl, triphenylmethyl, trialkylsilyl, trichloroethylcarbamate, trichloroethyoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and the butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

Purification of the compounds of the Formula I is preferably carried out by treating with pyridine and pivalic anhydride in a solvent such as DMF, THF, DMA, EtOAc, or the like to obtain a compound of the Formula I wherein $R_2$ is NHR" wherein R" is $(CH_3)_3C—C(O)—$, and X and R are as defined above.

This pivalylamido compound is then treated with sodium hydroxide, preferably with 1.0 N NaOH, in a solvent such as methanol, ethanol, or the like at from 0° C. to 80° C., preferably at about 24° C., for from ½ hour to 5 days, preferably for about 4 days. The solution is then acidified and treated to isolate the products by conventional means such as extraction, distillation, crystallization, chromatography, and the like.

The salts of compounds of Formula I described above are prepared by reacting the appropriate base with a stoichiometric equivalent of the acid compounds of Formula I to obtain pharmacologically acceptable salts thereof.

The compounds of this invention may also exist in hydrated or solvated forms.

The novel processes in steps beginning with (B) and continuing through (A) above may be conducted in a one-part process.

DETAILED DESCRIPTION

The compounds of Formula I and intermediates of Formula II of the present invention exist in tautomeric forms as purines or guanines as illustrated below. Both forms are included as part of the invention and are indiscriminately described in the specification.

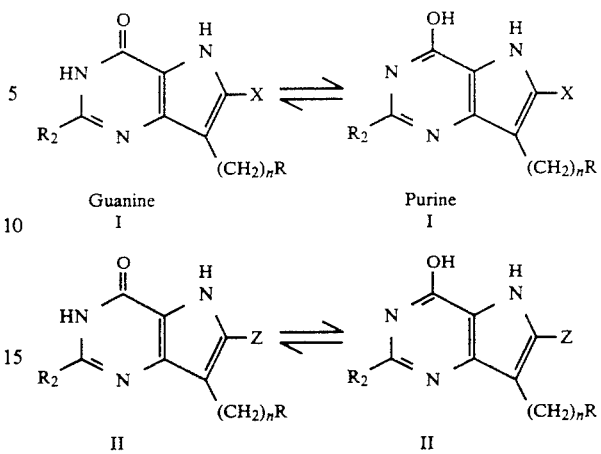

Guanine I   Purine I

II   II

The term "alkyl of one to four carbon atoms" means a straight or branched hydrocarbon chain up to four carbon atoms such as, for example, methyl, ethyl, propyl, isopropyl butyl, isobutyl, secondary butyl, or tertiary butyl. "Alkoxy of one to four carbon atoms" includes methoxy, ethoxy, propoxy, butoxy, and isomers thereof. Halogen is fluorine, chlorine, bromine, or iodine. Acyl of from two to six carbons is meant to include straight and branched chain, for example, acetyl, propionyl, butyryl, pivalyl, and the like.

The optionally substituted cyclic group recited for the R group of the above formula includes aromatic, heteroaromatic, alicyclic, and heteroalicyclic groups, preferably containing five to nine atoms. Preferred optional substituents include halogen, hydroxy, alkoxy, alkyl, and trifluoromethyl. Exemplary substituents include chloro, fluoro, methoxy, ethoxy, propoxy, butoxy, methyl, ethyl, propyl, and butyl. Halogen is bromo, iodo, chloro or fluoro. Preferred heteroatoms include oxygen, nitrogen, and sulfur, which can be present in combination in the same group. The preferred aromatic is phenyl, optionally substituted by halogen, alkyl of from one to four carbon atoms, hydroxy, alkoxy of one to four carbon atoms or trifluoromethyl. Heteroaromatic groups are 2- or 3-thienyl; 2- or 3 furanyl; 2-, 3-, or 4-pyridinyl; 2- or 3-pyrrolyl; 2-, 4-, or 5-thiazolyl; 2-pyrazinyl; 3- or 4-pyridazinyl; and 3-, 4-, or 5-pyrazolyl and more preferred as 3-thienyl. The preferred alicyclic and heteroalicyclic groups are 1- or 2-adamantyl, cyclohexyl, cycloheptyl, 2- or 3-tetrahydrofuranyl, 2- or 3 tetrahydrothienyl, 2- or 3-tetrahydropyranyl, 2-, 3-, or 4-piperidinyl, 3- or 4-pyrazolidinyl, 2-, 4-, or 5-thiazolidinyl, 2 or 3-piperazinyl, 2- or 3-morpholinyl, or 3- or 4-hexahydropyridazinyl.

The compounds of Formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid, and organic acids such as methanesulfonic acid, benzenesulfonic acid, p toluenesulfonic acid, isothienic acid, and the like, giving the hydrochloride, sulfate, methanesulfonate, benzene sulfonate, p-toluenesulfonate, and the like, respectively, or those derived from bases such as suitable inorganic and organic bases. Examples of suitable inorganic bases for the formation of salts of compounds of this invention include the hydroxides of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, and triethanolamine; amino acids such as arginine and lysine; guanidine; N methylglucamine; L-glutamine; N methylpiperazine; morpholine; ethylenediamine; N-benzylphenethylamine; tris(-hydroxymethyl)aminomethane; and the like. (See, for example, "Pharmaceutical Salts", *J. Pharm. Sci.* (1977) 66(1):1–19.)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

A preferred embodiment of the present invention is a compound of Formula I wherein $R_2$ is $NH_2$ or H, n is one, and R is either phenyl or 2- or 3 thienyl preferably 3-thienyl. A more preferred embodiment is 2 Amino-6-chloro-3,5-dihydro-7-(3-thienylmethyl)-4H pyrrolo[3,2-d]pyrimidin-4-one, 2 Amino-6-fluoro-3,5-dihydro-7-(3-thienylmethyl)-4H pyrrolo[3,2-d]pyrimidin-4-one;

and also the above compounds wherein $R_2$ is H.

Of these the most preferred is the 2-Amino-6-fluoro-3,5-dihydro-7-(3-thienylmethyl)-4H-pyrrolo[3,2-d]pyrimidin-4-one.

The compound of Formula I may generally be prepared according to the method shown in the following scheme.

SCHEME I

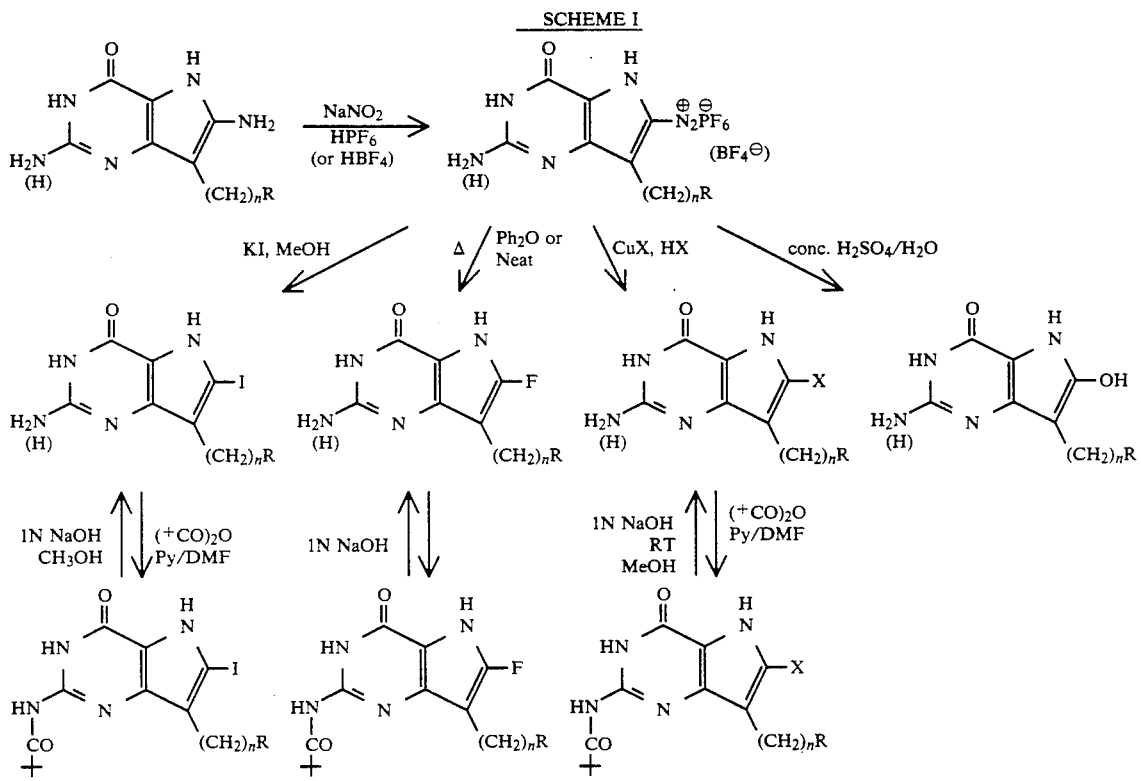

The compounds having the Formula I of the present invention have been shown to exhibit significant enzyme inhibition activity and accordingly selective inhibition of T-cell development. In the purine nucleoside phosphorylase (PNP-4) enzyme assay, an $IC_{50}$ is achieved at a dose of about from 0.9 to 3.18 micromoles on selected compounds of the present invention. PNP-4 activity for the compounds of Formula I is measured radiochemically by measuring the formation of [$^{14}$-C]-hypoxanthine from [$^{14}$-C]inosine [*Biomedicine* 33:39 (1980)]using human erythrocyte as the enzyme source. An in vivo inhibition of purine nucleoside phosphorylase (HPLC-1) enzyme assay is used essentially as disclosed in the *Annals of New York Academy of Sciences* 451:313 (1985) to further show the activity of the compounds of Formula I of the present invention. The same compounds also are found by a standard test (HTBA-1) [*Science* 214:1137 (1981)]to be selectively cytotoxic for T-cells in the presence of 2'-deoxyguanosine demonstrating utility for the compounds of Formula I as described herein. Since removal of T-cells or modulation of T-cells are beneficial in the treatment of autoimmune diseases, these compounds being selectively cytotoxic to T-cells will, therefore, be useful in their treatment. 8-Aminoguanosine, a known PNP-inhibitor, has been shown to be efficacious for inhibiting rejection of skin graft in dogs [J. B. Benear, et al, *Transplantation* 41:274 (1986)]. Clinically it has been shown that modulation and/or removal of T-cells by thoracic duct drainage, lymphapheresis, or total lymphoid irradiation gave partial to complete relief from rheumatoid arthritis in patients who were totally refractory to other forms of therapy [A. Tanay, et al, *Arthritis and Rheumatism* 30(1):1 (1987); S. Strober, et al, *Annual of Internal Medicine* V-102(4):441–449 (1985); H. G. Nusslein, et al, *Arthritis and Rheumatism* V-28(11):1205–1210 (1985); E. Brahn, et al, ibid V-27(5):481–487 (1984); and J. Karsh, et al, ibid V 24(7):867–873. (1981)]. Cyclosporin A, a T-cell modulator, showed beneficial effects in the treatment of juvenile diabetes (A. Assan, et al, *The Lancet*, January 12, p. 67 (1985). Additionally, cyclosporin A is presently the drug of choice for the prevention of transplant rejection (R. M. Merion, et al, *New Eng. J. Med.* 148 (1984). More recently, cyclosporin A is shown to be useful to treat psoriasis. Further, it is suggested the cyclosporin therapy is shown to markedly reduce activated T-cells in psoriatic lesions. Therefore, it is reasonable to believe the basis of the successful treatment of psoriasis is modulation of T-cell activity (see C. N. Ellis, et al, *JAMA* V-256(22):3110–3116 (Dec. 12, 1986). Finally, cyclosporin A is shown to be efficacious in rheumatoid arthritis (M. E. Weinblatt, et al, *Arthritis and Rheumatism* V-30(1):11–17 (January, 1987); O. Forre, et al, *Arthritis and Rheumatism* V-30(1):88–92 (January, 1987); M. Dougados, et al, *Arthritis and Rheumatism* 30(1):83–87 (January, 1987).

Representative examples from the present invention are shown in the following activity table to provide the activity discussed above.

ACTIVITY TABLE

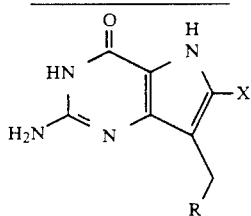

| Number | X | PNP-4 IC$_{50}$ ($\mu$M) |
|---|---|---|
| 3 | Br | 6.9 |
| 5 | I | >30 |
| 6 | Cl | 2.77 |
| 8 | F | 0.15 |

In vivo studies based on the above-noted disclosures may be used to determine activity in the particular disease states noted.

Since T-cells play a central role in immune response, use of the compounds of the invention is contemplated for the immunoregulation to prevent rejection in transplantation or in the treatment of psoriasis and in the treatment of autoimmune disease such as rheumatoid arthritis, systemic lupus erythematosus, inflammatory bowel disease, multiple sclerosis, myasthenia gravis, gout or gouty arthritis, juvenile diabetes, cancer, which is advantageously affected by agents cytotoxic to T-cells, and viral diseases which are advantageously affected by agents cytotoxic to T-cells either alone or in combination with an appropriate treatment thereof. The present invention thus includes compositions containing a compound of Formula I in treating rejection of transplantation or disease such as psoriasis in humans or autoimmune disease characterized by abnormal immune response in primates or humans. According to this aspect of the invention, the properties of the compounds of the invention are utilized by administering to a warm-blooded animal an effective amount of a pharmaceutical composition containing as the active ingredient at least about 0.1 percent by weight, based on the total weight of the composition of at least one such compound of the invention.

Pharmaceutical compositions of the invention can be formulated in any suitable way, preferably with an inert carrier for administration orally, parenterally, ophthalmically, topically, or by suppository.

For example, the compounds of the present invention are formulated into dosage forms such as tablets or syrups by blending with an inert pharmaceutical carrier such as lactose or simple syrup by methods well known in the art. For injectable dosage forms, they are formulated with vehicles such as water, propylene glycol, peanut oil, sesame oil, and the like. In these dosage forms, the active ingredient is from about 0.05 grams to 0.5 grams per dosage unit.

The present invention is further illustrated by way of the following examples.

EXAMPLE 1

2-Amino-6-diazonium-3,5-dihydro-7-(3-thienylmethyl)-4H-pyrrolo[3,2-d]pyrimidin-4-one hexafluorophosphate 2,6-Diamino-3,5-dihydro-7-(3-thienylmethyl) 4H-pyrrolopyrimidin-4 one (3.15 g; 10 mM) is dissolved in 75 mL of MeOH and cooled in an ice/acetone bath (the reaction is carried out in a plastic vial). Ten mL of HPF$_6$ is added to the reaction mixture and stirred. An aqueous solution of NaNO$_2$ (1.0 g in 1.0 mL of water) is slowly added to the reaction mixture while stirring when the mixture turned orange. The reaction mixture is stirred at 0° C. for 30 minutes when the product precipitates out. The product is collected by filtration, washed with ether, and dried in a vacuum oven at 25° C. overnight. Yield 4.0 g (95.6%).

EXAMPLE 2

2-(Pivalylamido)-6-bromo-3,5-dihydro-7-(3-thienylmethyl)-4H-pyrrolo[3,2-d]pyrimidin-4-one The diazonium salt (2.5 g), prepared as in Example 1, is dropped into a hot solution of CuBr (3.0 g)/HBr (5.0 mL)/water (40 mL), heated on a steam bath at 70° C. After the addition is complete, the reaction mixture is heated in the water bath for an additional 1 hour. The reaction mixture is filtered and the filtrate is evaporated to dryness under vacuum. The crude residue is dissolved in toluene and the last trace of water is removed by distillation under vacuum. The residue is dried under vacuum for 24 hours. The crude product is dissolved in DMF (30 mL and then treated with pyridine (2.0 mL) and pivalic anhydride (3.0 mL) and the reaction mixture is stirred at 24° C. for 24 hours. The solvent is removed under vacuum and the residue is extracted with EtOAc. The EtOAc extract is washed with brine, followed by NaHCO$_3$ solution and then dried (MgSO$_4$) and evaporated to dryness give the crude product which is flash chromatographed using 1:1 hexane/EtOAc as eluent to give the desired product as faster moving spot. Yield 0.25 g (10%). It is rechromatographed to get analytical sample; mp>240° C.

EXAMPLE 3

2-Amino-6-bromo-3,5-dihydro-7-(3-thienylmethyl)-4H-pyrrolo[3,2-d]pyrimidin-4-one 7-Bromo-pivalylamido compound (0.45 g) in Example 2 is dissolved in MeOH (30 mL) and then treated with 1.0 N NaOH (30 mL) and stirred at 24° C. for 4.0 days. The solution is carefully acidified with concentrated HCl and the solid product is collected by filtration. The crude product is washed with ether and then chromatographed using $CHCl_3$-5%MeOH as eluent to give the pure product as partial HCl and partial hydrate. Yield 120 mg (33.6%); mp>240° C.

EXAMPLE 4

2 (Pivalylamido)-6-iodo-3,5-dihydro-7-(3-thienylmethyl)-4H-pyrrolo[3,2-d]pyrimidin-4-one The diazonium salt (1.0 g) from Example 1 is suspended in MeOH (25 mL) and an aqueous solution of KI (2.0 g in 10.0 mL) is added to the mixture at 24° C. and then stirred for 2 days. The solvent is removed under vacuum and the residue is dissolved in DMF (25 mL), treated with pivalic anhydride (3.0 mL) and pyridine (2.0 mL), and then stirred at 24° C. for 24 hours. DMF is removed under reduced pressure and the residue is extracted with EtOAc. The EtOAc extract is washed with brine, $NaHCO_3$ solution, 5% HCl, water, and sodium thiosulfate, and dried ($MgSO_4$). Removal of the solvent gives the crude product which is chromatographed over silica gel using 1:1 hexane-EtOAc as eluent. The faster moving spot is isolated as the desired product. Yield 0.08 g (7.3%); mp>240° C.

EXAMPLE 5

2-Amino-6-iodo-3,5-dihydro-7-(3-thienylmethyl)-4H-pyrrolo3,2-d]pyrimidin-4-one

7-Iodo-pivalylamido compound (0.07 g) in Example 4 is dissolved in MeOH (10 mL) and 1 N NaOH solution (5 mL) and the mixture is stirred at 24° C. for 4 days. The reaction mixture is carefully acidified with concentrated HCl and the precipitated product is filtered, washed with water, and dried overnight at 24° C. under vacuum to give the desired product which contains 0.7 HCl and 1.25 $H_2O$. Yield 43 mg (82%); mp>260° C.

EXAMPLE 6

2-Amino-6-chloro-3,5-dihydro-7-(3-thienylmethyl)-4H-pyrrolo[3,2-d]pyrimidin-4-one The diazonium salt (2.30 g) from Example 1 is slowly added to a hot solution of CuCl (2.50 g) in concentrated HCl (5.0 mL) and water (20 mL) at 75° C. The reaction mixture is heated on a steam bath for 30 minutes when it turned black. The mixture is filtered and the filtrate is evaporated to dryness. The crude product is extracted with MeOH several times and the total extracts are combined and evaporated to dryness. The residue is dissolved in DMF (50 mL) and then treated with pivalic anhydride (4.0 mL) and pyridine (20 mL) and the mixture is stirred at 24° C. for 24 hours. The reaction mixture is evaporated to dryness and the residue extracted with EtOAc as usual and chromatographed over silica gel using 1:1 hexane EtOAc as eluent. The product obtained from the column is found to contain some pivalic anhydride, so it is dissolved in MeOH (5.0 mL) and IN NaOH (3.0 mL) and stirred at 24° C. for 3 days. The reaction mixture is neutralized with 5% HCl when the product is precipitated out. The mother liquor on concentration gives an additional amount of product. The product is recrystallized from MeOH to give analytical sample as monohydrochloride, monohydrate. Yield 20 mg; mp>240° C.

EXAMPLE 7

2-Amino-6-diazonium-3,5-dihydro-7-(3-thienylmethyl)-4H-pyrrolo[3,2-d]pyrimidin-4-one tetrafluoroborate 2,6-Diamino-3,5-dihydro-7-(3-thienylmethyl) 4H-pyrrolopyrimidin-4-one (11.06 g; 35.11 mM) is suspended in 50 mL of MeOH and cooled in an ice/acetone bath (the reaction is carried out in a plastic vial). Forty-eight percent $HBF_4$ (15 mL) is added to the suspension followed by $NaNO_2$ (5.0 g; 72.46 mM) in 20 mL water. The reaction mixture is allowed to stand at 0° C. for an additional 20 minutes when a yellow ppt is formed which is filtered, washed with ether, and dried under vacuum at 24° C. for 24 hours; yield 15.75 g.

EXAMPLE 8

2-Amino-6-fluoro-3,5-dihydro-7-(3-thienylmethyl) 4H-pyrrolo[3,2-d]pyrimidin-4 one 2-Amino 6-diazonium 3,5-dihydro-7-(3-thienylmethyl)-4H-pyrrolo[3,2-d]pyrimidin-4-one tetrafluoroborate (15.75 g) is heated at 200° C. on a preheated heating bath for 1 minute when a vigorous evolution of gas occurred. The cooled reaction product is extracted with methanol and concentrated and adsorbed on dry silica gel. A portion of the compound-silica gel mixture is loaded onto a prepacked column and flash chromatographed using acetone/5% methanol as eluent. The fluoro-compound is isolated along with some faster and slower moving compounds. It is rechromatographed over silica gel to give the pure product. Yield 100 mg; mp>240° C. $^{19F}$NMR shows signal at −129 ppm. RF=0.5 ($SiO_2$, $CHCl_3$-MeOH (4:1)).

We claim:

1. A compound of the Formula (I)

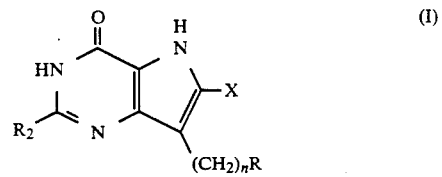

or a pharmaceutically acceptable acid addition or base salt thereof, wherein
   (1) $R_2$ is (a) hydrogen, (b) NHR' wherein R' is (i) hydrogen, or (ii) alkyl, or (c) NHR" wherein R" is acyl of two to six carbons;
   (2) n is an integer of zero through four;
   (3) X is F, Cl, Br, I, or OH; and
   (4) R is phenyl optionally substituted by chloro, fluoro, alkoxy or one to six carbon atoms, or alkyl of one to six carbon atoms, or 3-thienyl.

2. A compound of claim 1 wherein n is one.
3. A compound of claim 2 wherein $R_2$ is $NH_2$.
4. A compound of claim 2 wherein $R_2$ is hydrogen.
5. A compound of claim 2 wherein $R_2$ is NHR' or NHR".
6. A compound of claim 2 wherein X is chloro.
7. A compound of claim 2 wherein X is OH.
8. A compound of claim 2 wherein X is F.

9. A compound of claim 2 wherein R is phenyl optionally substituted by chloro, fluoro, alkoxy of one to six carbon atoms, or alkyl of one to six carbon atoms.

10. A compound of claim 2 wherein R is 3-thienyl.

11. A compound of claim 10 which is 2-(pivalylamido)-6-bromo-3,5-dihydro-7-(3-thienylmethyl)-4H-pyrrolo[3,2-d]pyrimidin-4-one.

12. A compound of claim 10 which is 2-amino-6-bromo-3,5-dihydro-7-(3-thienylmethyl)-4H-pyrrolo[3,2-d]pyrimidin-4-one.

13. A compound of claim 10 which is 2-(pivalylamido)-6-iodo-3,5-dihydro-7-(3 thienylmethyl)-4H-pyrrolo[3,2-d]pyrimidin-4-one.

14. A compound of claim 10 which is 2-amino-6-iodo-3,5-dihydro-7-(3-thienylmethyl)-4H-pyrrolo-[3,2-d]pyrimidin-4-one.

15. A compound of claim 10 which is 2-amino-6 chloro-3,5-dihydro-7 (3-thienylmethyl)-4H-pyrrolo[3,2-d]pyrimidin 4-one.

16. A compound of claim 10 which is 2-amino-6-fluoro-3,5-dihydro-7-(3-thienylmethyl)-4H-pyrrolo[3,2-d]pyrimidin-4-one.

17. A pharmaceutical composition for treating a condition or disease advantageously affected by an agent cytotoxic to T-cells which comprises a cytotoxic to T-cell effective amount of a compound of claim 1 and a pharmaceutically acceptable carrier.

18. A method of treating a condition or disease advantageously affected by a cytotoxic to T-cell agent in a host suffering from the condition or disease which comprises administering to said host a pharmaceutical composition as claimed in claim 17.

* * * * *